United States Patent [19]

Neufeld et al.

[11] Patent Number: 5,032,575
[45] Date of Patent: Jul. 16, 1991

[54] METHOD FOR ENHANCING HEALING OF CORNEAL ENDOTHELIAL WOUNDS

[75] Inventors: Arthur H. Neufeld, Newton Highlands; Nancy C. Joyce, Sudbury, both of Mass.; Marcia M. Jumblatt, Louisville, Ky.

[73] Assignee: Eye Research Institute of Retina Foundation, Inc., Boston, Mass.

[21] Appl. No.: 337,618

[22] Filed: Apr. 13, 1989

Related U.S. Application Data

[62] Division of Ser. No. 256,847, Oct. 12, 1988.

[51] Int. Cl.$^5$ ............................................. A61K 37/00
[52] U.S. Cl. ...................................................... 514/12
[58] Field of Search .......................................... 514/12

[56] References Cited

U.S. PATENT DOCUMENTS

4,559,343  12/1985  Han et al. .............................. 514/974
4,604,234  8/1986  Fujii et al. ................................ 514/2

FOREIGN PATENT DOCUMENTS

83306676.4  5/1985  European Pat. Off. .
86107343.5  5/1985  European Pat. Off. .
59-65020  1/1984  Japan .

OTHER PUBLICATIONS

Neufeld et al., Invest. Ophthal. Vis. Sci., 26(10) 1437–1442 (1986).
Jumblatt et al. Invest. Opthal. Vis. Sci., 29(4): 586–593 (Apr. 1988).
Burstein, N. L., J. Ocular Pharm. 3(3) 263–277 (1987).
Singh et al., Amer. J. Ophthal. 103(6) 802–807 (1987).
Van Brunt and Klausner, *Biotechnology* 6(1), 25–30 (Jan. 1988).
Chiron Ophthalmics, "Epidermal Growth Factor", Product Brochure (date unknown, no earlier than 1987–1988).
Tsutsumi, et al., *J. Clin. Invest.* 81(4), 1067–1071 (Apr. 1988).
Singh and Foster, *Amer. J. Ophthal.* 103(6), 802–807 (1987).
Petroutsos, et al., *Ophthalmic Res.* 18, 299–300 (1986).
Watanabe, Iu Igakuzassi 36(1), 1–8 (1984), *Chem. Abstr.* 103:207534t, 1985.
Watanabe, et al., *Atarashii Ganka* 1(5), 681–684 (1984) (Chem. Abstr. 102:126333d 1985).
Woost et al., Exp. Eye Res. 40, 47–60 (1985).
Neufeld et al., Invest. Ophthal. Vis. Sci., (26)10:1437–1442 (1986).
Raymond et al., Invest. Ophthal. Vis. Sci. (27)4:474–479 (1986).

*Primary Examiner*—Stanley J. Friedman
*Assistant Examiner*—Zohreh A. Fay
*Attorney, Agent, or Firm*—Kilpatrick & Cody

[57] ABSTRACT

Method using a non-steroidal antiinflammatory compound, such as indomethacin and/or a growth factor that causes a change in cell function when bound to a specific cell surface receptor, such as epidermal growth factor (EGF), to enhance healing and restore function of the corneal endothelium. The compositions can be administered alone, in combination, or in sequence, before or after injury, for example, in an irrigation solution or in combination with a nutritive solution for storage of a cornea prior to transplant.

Examples of useful growth factors include, in addition to EGF and EGF-like compounds, fragments of EGF containing the receptor binding region, and EGF modified to improve stability, increase half-life, or enhance permeation into the eye. Examples of other non-steroidal antiinflammatories include aspirin, ibuprofen, and suprofen. The composition can be applied topically to the eye or delivered in a controlled fashion by means of a material such as a polymeric implant, gel, or liposomes.

The effective dosage is that amount which promotes closure of corneal endothelial tissue and restores function, i.e., restores permeability, including both barrier function and pumping function.

11 Claims, 4 Drawing Sheets

METHOD FOR ENHANCING HEALING OF CORNEAL ENDOTHELIAL WOUNDS

This is a divisional of U.S. Ser. No. 07/256,847, "Method for Enhancing Healing of Corneal Endothelial Wounds" Filed on Oct. 12, 1988, by Arthur H. Neufeld, Nancy C. Joyce, and Marcia M Jumblatt, now pending.

BACKGROUND OF THE INVENTION

This invention is generally in the area of ophthalmic compositions and more specifically relates to a method and compositions for enhancing healing of injuries to the corneal endothelium.

The corneal endothelium, a single layer of hexagonal cells at the boundary between the fluid-filled anterior chamber and the clear collagenous stroma at the posterior surface of the cornea, is critical for the maintenance of transparency of the tissue. The cell layer is avascular, lacks innervation, and is bathed on its apical face by aqueous humor. In the aging human, the density of corneal endothelial cells gradually decreases and the remaining cells retain their polygonal shape while becoming wider and thinner to maintain a permeability barrier. When a wound or discontinuity occurs in this tissue, the cells bordering the defect become elongated, migratory, and, perhaps, synthesize new extracellular matrix material.

Clinically significant dysfunctions of the endothelium, due to cell loss associated with dystrophies or degenerations caused by ocular diseases, drugs, trauma or surgery, are responsible for the majority of corneal transplants. Despite its physiologic importance, the corneal endothelium is an extremely fragile tissue. Since the endothelium is relatively amitotic in the adult human, repair to areas of injury is via migration and spreading of neighboring cells to cover the defect in the monolayer. At low cell densities, these repair mechanisms may be insufficient to restore the endothelium to full physiologic function. If the endothelial barrier and pump functions become compromised, water enters the stroma and disrupts the precise arrangement of collagen fibrils, eventually resulting in visual impairment.

Upon disruption of the endothelial barrier, undamaged cells break their junctional complexes, elongate and migrate to fill denuded areas. These areas of repair are characterized by stromal edema. Following repopulation of the area, cells reform their junctions, resume their hexagonal shape, and regain their ability to act as a permeability barrier, with subsequent resolution of corneal edema.

The corneal endothelium has been characterized biochemically, physiologically and ultrastructurally. Features include abundant NA/K ATPase, adenylate cyclase activity, cyclooxygenase/lipooxygenase pathways, EGF and $\beta$-adrenergic receptors, phenotypically controlled synthesis of type IV collagen, active fluid secretion coupled to bicarbonate transport, gap junctions, maculae occludens and highly organized circumferential bundles of f-actin.

Currently, medical management of endothelial cell loss and dysfunction is limited, and research aimed at developing drug treatments is impeded by the lack of suitable experimental models for human tissue.

Studies of the events of wound closure in tissue culture systems, even using rabbit cells which, unlike human cells, are mitotically active, allow independent observation of changes in cell shape, migration, metabolism, and proliferation. The rabbit corneal endothelium is not an ideal model because of its relatively high mitotic rate compared to human tissue. Nevertheless, the use of rabbits to study wound closure of the corneal endothelium has led to significant observations on cellular shape changes during migration as well as changes in tissue permeability and pump function during healing. Furthermore, comparing the mitotic abilities of rabbit and human endothelium may provide insight into the amitotic state of human tissue.

Studies using cultured rabbit corneal endothelial tissue were reported in *Invest. Octhalmol. Vis. Sci.* 25, 1235 (1984) by Neufeld, et.al., *Invest. Octhalmol. Vis. Sci.* 27(10), 1437-1442 (October 1986) by Neufeld, et.al., and *Invest. Opthalmol. Vis. Sci.* 27(4), 474-479 (April 1986) by Raymond, et.al.. The studies reported in the 1984 paper demonstrated that cultured rabbit endothelial cells, like the native tissue, synthesizes cyclic AMP L in response to $\beta$-adrenergic stimulation. The mitogenic and morphological responses of cultured rabbit tissue to epidermal growth factor (EGF), a well-defined growth factor which stimulates bovine, feline, and perhaps human corneal endothelial proliferation, were studied and reported in the April 1986 paper. EGF was found to induce a shape change in the cells that is independent of mitosis. It was postulated that the shape changes were similar to that found in migrating cells closing a wound. EGF-induced elongation was reversible, independent of EGF-stimulated mitosis, and similar to the elongation of migratory cells adjacent to experimental endothelial injuries. It was hypothesized that EGF exerts its effect via a specific receptor and can increase phosphotidyl inositol turnover and subsequent synthesis of arachidonic acid metabolites.

These studies indicated that epidermal growth factor (EGF) and/or indomethacin (INDO) cause elongation in first passage cultures of rabbit and human corneal endothelial cells and that addition of exogenous prostaglandin $E_2$ ($PGE_2$) to cultures treated with EGF and indomethacin blocks elongation, i.e., the cells retain their polygonal shape. As cultures of polygonal endothelial cells synthesize abundant $PGE_2$ and this synthesis is totally inhibited by indomethacin, it was concluded that i endogenous synthesis of $PGE_2$ is necessary for maintenance of normal endothelial cell shape.

Epidermal growth factor (EGF) is an acidic, low molecular weight protein originally purified from mouse submaxillary gland which was initially identified because of its ectodermal effects on new-born mice, causing premature eyelid opening and incisor eruption. EGF is a 53-residue polypeptide of 6,045 Daltons, with three cysteine-cysteine linkages. Three amino acids are completely absent from its structure: lysine, alanine, and phenylalanine. EGF has been shown to stimulate proliferation of corneal epithelium in organ culture and in vivo. Recently, EGF has also been shown to stimulate proliferation of cultured corneal endothelial cells in organ culture.

While these findings are interesting, they do not provide a method for controlling and enhancing repair and restoration of normal functioning of the corneal endothelium in the human eye.

It is therefore an object of the present invention to provide methods for enhancing and controlling repair and restoration of function of the human corneal endothelium.

It is a further object of the present invention to provide compositions for the manipulation of the healing process and restoration of the corneal endothelium's function as a permeability barrier.

SUMMARY OF THE INVENTION

Method using a non-steroidal anti-inflammatory compound, such as indomethacin, and/or a growth factor that causes a change in cell function when bound to a cell surface receptor, such as epidermal growth factor (EGF), to enhance healing and restore function of the corneal endothelium. The compositions can be administered alone, in combination, or in sequence, before or after injury, for example, in an irrigation solution, prior to or during cataract surgery, or in combination with a nutritive solution for storage of the cornea prior to transplant.

Examples of useful growth factors include, in addition to EGF and EGF-like compounds, fragments of EGF containing the receptor binding region, and EGF modified to improve stability, increase half-life, or enhance permeation into the eye. Examples of other non-steroidal anti-inflammatories include aspirin, ibuprofen, and suprofen.

The composition can be applied topically to the eye or delivered in a controlled fashion by means of a material such as a polymeric implant, gel, or liposomes.

The effective dosage is that amount which promotes closure of corneal endothelial tissue and restores function, i.e., restores permeability, including both barrier function and pumping function. The dosage for each compound is based in part on the method of administration, and will be varied according to the half-life and rate of absorption of the compound, as well as its specific biological activity. Clinically, function is measured by determining the clarity of the cornea and degree of swelling. The effective dosage of indomethacin in a nutritive or irrigating solution is between about 0.1 and 50 $\mu$M, preferably 10 $\mu$M, and between about 0.1 M and a saturated suspension for topical application. The effective dosage of EGF in a nutritive or irrigation solution is between about one and 50 ng EGF/ml, preferably 10 ng. EGF cannot be applied topically unless in a vehicle or form which allows passage of active compound through the surface layers of the cornea to the underlying corneal endothelium.

DETAILED DESCRIPTION OF THE INVENTION

Figure 1:
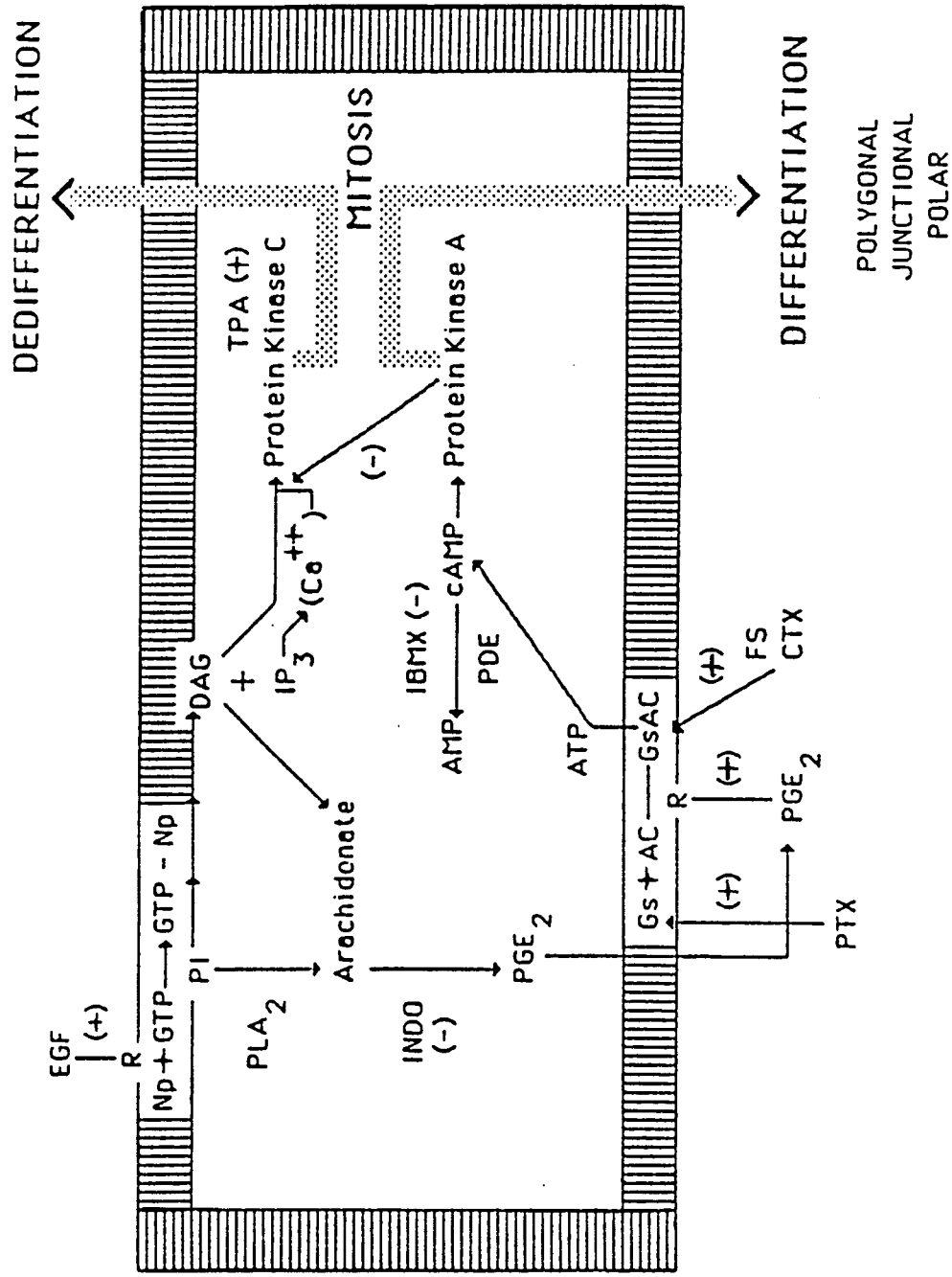
FIG. 1 is a schematic representation of intracellular pathways regulating corneal endothelial cell differentiation. Np, coupling protein; GTP, guanosine triphosphate; PLA$_2$, phospholipase A$_2$; DAG, 1,2 diacylglycerol; IP$_3$, myoinositol 1,4,5 triphosphate; PDE, phosphodiesterase; AMP, adenosine monophosphate, ATP, adenosine triphosphate; cAMP, adenosine 3',5' monophosphate; Gs, stimulating guanine nucleotide binding protein; AC, adenylate cyclase.

During and following surgery, or when any change in corneal homeostasis occurs, there is an injury like response, accompanied by shape changes resulting from migration and spreading of the cells. However, shape change is not the same as healing. There are at least four classes of compounds that cause a change in cell shape that is not related to healing. For example, cytochalasin causes a shape change by depolymerization of actin, which inhibits healing. Colchisine alters cell shape but inhibits mitosis. Sulfhydral reagents and chelating agents also alter cell shape but do not affect healing.

The present invention is the discovery that two types of compounds, growth factors specific for cell surface receptors that cause a change in cell function and non-steroidal anti-inflammatory compounds, which also affect cell shape, can be used to promote closure of corneal endothelial tissue and restore function of the corneal endothelium. Function of the corneal endothelium is restored when the thin layer of cells again serves as a permeability barrier, with ions and water being transferred into and out of the cells as required to maintain the corneal intrastructure.

When the cells are serving as an effective barrier, the cornea is clear and not swollen. Clarity is determined clinically using techniques such as observation with a slit lamp or by specular microscopy. Swelling can be measured by pachymetry or other methods known to those skilled in the art.

Administration of a growth factor such as EGF to corneal endothelial cells enhances the migratory response of cells to wounding, probably via the phosphoinositol pathway and protein kinase-C activation. EGF is used herein to include EGF, EGF-like growth factors and other growth factors which bind to a cell surface receptor such as the EGF receptor to alter cell function. Synthesis of prostaglandin E$_2$, which appears to be involved in the maintenance of polygonal shape, is inhibited by treatment with a non-steroidal anti-inflammatory, such as the cyclooxygenase inhibitor, indomethacin, resulting in elongation of cells in a manner similar to that observed in wound healing. In combination, there is a mixture of cellular responses, including an increase in the number of migrating cells within the wound area as well as stimulation of spreading of cells and maintenance of cell-cell contact during wound closure, which can be manipulated as a function of the dosage of each compound and the time of administration relative to the injury to enhance healing and restoration of corneal endothelium function.

Clinically, manipulation of the timing of EGF and indomethacin treatment is possible using the enhanced migratory response of cells at the beginning of treatment and the enhanced spreading of cells and maintenance of cell-cell contact as the defect closes. For example, different effects can be achieved by administering EGF, then indomethacin, or vice versa, or by treatment with just EGF or indomethacin.

The compositions can be applied topically to the eye or delivered in a controlled fashion by means of a material such as a polymeric implant, gel, or liposomes.

Corneas can be treated directly using a nutrient storage solution prior to transplantation, or during surgery using an irrigation solution, to help maintain endothelial integrity and function. Nutritive solutions are used for storage of corneas, for example, during eye bank storage. Although nutrients in the storage solution are not required for the compositions of the present invention to be effective, they are preferred. An irrigating solution is a solution used during intraocular surgery, for example, to wet the cornea, to maintain structures, and to prevent damage to other tissues.

The effective dosage is that amount which promotes closure of corneal endothelial tissue and restores function, i.e., restores permeability, including both barrier function and pumping function. The dosage for each compound is based in part on the method of administration, and will be varied according to the half-life and rate of absorption of the compound, as well as its specific biological activity. The effective dosage of indomethacin in a nutritive or irrigating solution is between about 0.1 and 50 $\mu$M, preferably 10 $\mu$M, and between about 0.1 M and a saturated suspension for topical application. The effective dosage of EGF in a nutritive or irrigation solution is between about one and 50 ng EGF/ml, preferably 10 ng. The indomethacin and EGF can both be administered alone or in combination with each other. However, EGF cannot be applied topically unless in a vehicle or form which allows passage of active compound through the surface layers of the cornea to the underlying corneal endothelium. The carrier solutions are not critical but must be compatible with the eye. For example, indomethacin is usually diluted into a phosphate buffer having a pH between 7 and 9.

The effective dosage can initially be determined from studies conducted in vitro on cultures of rabbit endothelial cells or on intact corneal buttons, using alterations in morphology as a primary indicator of healing. Confirmation of the effective dosage is then made using clinical studies. For example, addition of a solution containing 10 ng EGF/ml and 1 $\mu$M indomethacin to cells in culture causes a two times greater change in cell shape than in control cells. The EGF appears to stimulate cell migration while the indomethacin appears to enhance cell spreading in response to wounding. Treatment of the corneal cells prior to injury accelerates healing, wounds closing in 3 to 4 days as opposed to 7 to 8 days for controls.

The following non-limiting examples demonstrate how the compositions of the present invention is used to enhance healing of corneal endothelium and restoration of function, i.e. restoration of an effective permeability barrier.

EXAMPLE 1

Maintenance of corneal cell shape by Prostaglandin $E_2$ and the effects of EGF and Indomethacin The data in this example was reported by Jumblatt, et.al., in *Invest. Opthal. Vis. Sci.* 29(4), 586 (April 1988). Methods used are known to those skilled in the art, as reported by Jumblatt, et.al.

Confluent, rabbit corneal endothelial cells subcultured for seven days under normal conditions, in the absence of added indomethacin or EGF, are polygonal and morphologically resemble native tissue. The mean of the major axes of the polygonal shaped cells is 33 $\mu$ and the mean of the perimeters (Per) is 95 $\mu$. For an ideal, perfectly round cell, the ratio Per/$A_{max}$ should be equal to (x) (3.14). In the presence of EGF, the corneal endothelial cells become elongated. Within seven days, the endothelial cells are spindle-shaped at confluence and have a significantly greater distribution of major axes, although there is little or no effect on cell density. The ratio Per/$A_{max}$ decreases significantly, indicating loss of rotundness.

In the presence of indomethacin, the cells are elongated at confluence with a stellate shape. Continuity of cell borders is often lost. The distribution and means of the major axes increases, and the Per/$A_{max}$ ration of 2.6 indicates loss of the polygonal shape.

When corneal endothelial cells are cultured in the presence of EGF and indomethacin, marked elongation occurs to the extent of producing rod-shaped cells at confluence that bear little resemblance to their sister cultures grown under control conditions. The cells are fibroblastic in appearance and often form swirling patterns of dense populations. The mean of the major axes of these cells is approximately twice (60 $\mu$) that of control cells, and the frequency distribution of $A_{max}$ of these cells is skewed markedly to higher values. The decreased ratio Per/$A_{max}$ to 2.5 is characteristic of an elongated cell. Under these conditions, cell density is approximately one-third greater than cells grown under control conditions. Potentiation of EGF-induced elongation also occurs with $10^{-5}$ suprofen and, to a lesser extent, with equimolar flurbiprofen; a steroidal anti-inflammatory, dexamethasone, has no effect.

The addition of increasing concentrations of a synthetic analog of prostaglandin $E_2$ causes inhibition of the elongation of $A_{max}$ when cells are grown in the presence of EGF and indomethacin. Cells grown in the presence of EGF, indomethacin, and 0.5 $\mu$g/ml $PGE_2$ analogue are indistinguishable from cells grown in the absence of EGF and indomethacin. The addition of increasing doses of $PGF_{2\alpha}$ has no effect on the elongation of $A_{max}$ produced by the combination of EGF and indomethacin. When added in the absence of EGF, arachidonic acid had no effect on cell shape in the presence or absence of indomethacin.

Synthesis of $PGE_2$ by cultured corneal endothelial cells was measured by growing cells in the presence and absence of EGF and/or indomethacin. Under control conditions, cultured corneal endothelial cells synthesize and release substantial quantities of endogenous $PGE_2$. Synthesis of $PGE_2$ is unaffected by the addition of EGF. Indomethacin totally inhibits $PGE_2$ synthesis in control cultures and cultures to which EGF has been added.

The effect of indomethacin on corneal endothelial cell shape is greatly enhanced by EGF. Other cyclooxygenase inhibitors are also effective but less potent; the rank order of potency appears to be: indomethacin > suprofen > flurbiprofen. The inactivity of dexamethasone is consistent with a suggested lack of nuclear steroid receptors in these cells.

When the analogue of prostaglandin $E_2$ is included in the culture medium, the marked effect of EGF and indomethacin to induce elongation does not occur. This demonstrates that, if the cells are exposed to prostaglandin $E_2$, they retain their normal, polygonal shape. Under control conditions, when polygonal morphology is evident, corneal endothelial cells in culture endogenously synthesize prostaglandin $E_2$, as shown by the above results. When corneal endothelial cells are growing in culture under conditions which favor their normal, polygonal shape, synthesis of prostaglandin $E_2$ occurs and is necessary for maintenance of this shape. The presence of indomethacin blocks the formation of $PGE_2$ and the cells become stellate in shape.

In the presence of EGF, the corneal endothelial cells must synthesize another product, which influences the cells to elongate and become spindle-shaped. The action of the unknown product to favor the elongated shape is potentiated in the presence of indomethacin because synthesis of $PGE_2$, which favors polygonal shaped cells, is blocked. Thus, when the cyclooxygenase pathway is inhibited, the cells become even more fibroblastic-like.

Arachidonic acid is a common intermediate in this scheme that is apparently available under controlled culture conditions and made into prostaglandin $E_2$. In vivo. $PGE_2$ is synthesized by rabbit corneal endothelium. Arachidonic acid added to control media did not cause alteration of the normal polygonal cell shape indicating that sufficient material must have already been available for prostaglandin $E_2$ synthesis. If EGF liberates arachidonic acid which is made into another product that favors elongation, then arachidonic acid added to culture media containing indomethacin should have substituted for EGF. That this did not occur indicates that the effect of EGF is not mediated via arachidonic acid products, such as the lipooxygenase products generated following cryo-injury in vivo.

The spindle cell shape in the presence of EGF may not necessarily be related to the stellate cell shape in the presence of indomethacin. EGF may exert its effects through a change in the extracellular matrix which the cells secrete and on which they grow. Inhibition of the synthesis of prostaglandin $E_2$ causes a different cellular pattern which may not be related to changes in the extracellular matrix, but, rather, internal, cytoskeletal changes. Nevertheless, with both EGF stimulation and cyclooxygenase inhibition, the cells become extremely fibroblastic in appearance, forming typical swirling patterns on the culture dish. Furthermore, when indomethacin is present, neighboring cells often lose continuity of their cellular borders, which probably is reflected in increased permeability as compared to the control, polygonal cell monolayer.

EXAMPLE 2

Pharmacological Regulation of morphology and mitosis in cultured rabbit conenal endothelium Corneal endothelial cells grown in control culture medium for 1 week formed a monolayer of closely apposed polygonal cells, which, when reacted with rhodamine labelled phallacidin, exhibited bright circumferential bands of f-actin. Widely separated cables of somewhat smaller diameter were also seen within the cytoplasm of these cells. EGF treated cultures consisted of elongated cells which were characterized by actin fibers throughout the cytoplasm running roughly parallel to the long axis of the cell. Treatment with INDO resulted in elongated bipolar cells almost completely lacking in individual actin fibers, characterized instead by diffuse reticular staining throughout the cytoplasm. This diffuse actin staining pattern was even more obvious in cultures treated concurrently with EGF and INDO. However, circumferential actin bands and discrete cytoplasmic fibers were apparent in cultured cells grown in the presence of $PGE_2$ in addition to EGF and INDO.

Subcellular alterations of pharmacologically modulated endothelial phenotypes were examined by transmission electron microscopy. Corneal endothelial cells grown in control medium were characterized by apical junctional complexes, regions of submembrane microfilament organization near the basal surface, extensive rough endoplasmic reticulum and accumulation of extracellular material. Overlap of cytoplasmic processes was observed, but regions of nuclear overlap were absent. EGF-treated cultures were characterized by elongated cells which also demonstrated overlap of cytoplasmic processes and in which nuclear overlap was absent. Junctional complexes were absent. The cytoplasm of EGF-treated cells was distinctly lacking in polarization as evidenced by both apical and basal submembrane microfilaments. The cytoplasm contained predominantly smooth rather than rough endoplasmic reticulum. Cultures treated with INDO were characterized by extensive cytoplasmic overlap and close ajunctional apposition of the membranes of adjacent cells. Endoplasmic reticulum was largely of the smooth type and free ribosomes were often seen in the cytoplasm. Cultures treated with indomethacin and EGF were multilayered, with both cytoplasmic and nuclear overlap. Intracellular junctions were not observed, nor was there any apical/basal polarization of individual cells. Deposits of extracellular material were absent. The addition of synthetic $PGE_2$ to EGF- and INDO-treated cultures maintained the differentiated morphology of the polygonal cells. Ultrastructurally, junctional complexes, rough endoplasmic reticulum and basal distribution of submembrane microfilaments were observed. Some overlap of cytoplasmic processes was noted, but the cultures were predominantly monolayered.

The phorbol ester TPA, a direct activator of protein kinase C, was tested for its ability to mimic EGF and stimulate cellular elongation and/or mitosis. At a concentration of $10^{-8}$ M, TPA caused elongation of cultured corneal endothelial cells and increased cell density after 1 week in culture. When TPA and EGF were both present in the medium, synergistic effects were not noted. The addition of INDO, which independently causes some elongation, to TPA containing medium resulted in marked enhancement of cellular elongation similar to that seen with EGF and INDO, but had no effect on final cell density.

Because $PGE_2$ stimulates synthesis of cyclic AMP, other agents with similar activity were tested for their ability to prevent EGF+INDO-induced elongation and to restore polygonal cell shape. Cholera toxin, a direct activator of adenylate cyclase, added to control culture medium had no effect on cell shape and was not mitogenic. However, CTX antagonized EGF and INDO-induced elongation without preventing increased cell density in response to these agents. Forskolin and the phosphodiesterase inhibitor, isobutyl methylxanthine, also prevented EGF and INDO-induced elongation and inhibited endothelial mitosis.

Pertussis toxin, an inhibitor of guanine nucleotide regulatory protein, was added to culture medium to assess the role of G protein regulation of endothelial mitosis and cell shape. PTX alone had no effect on either parameter. In combination with either EGF for INDO, PTX restored polygonal cell shape without significantly altering cell density.

Additional studies focused on the interaction of the EGF-activated pathway with that of the cyclic AMP-mediated pathway. In the presence of CTX, EGF-induced elongation did not occur., Further, the mitogenic effect of EGF was potentiated by CTX and the resulting cultures consisted of a monolayer of small polygonal cells. However, CTX did not prevent elongation in response to TPA, but did, as noted above with respect to EGF, potentiate the mitogenic response of endothelial cells to this phorbol ester. Thus, the CTX-stimulated cyclic AMP-mediated step, which blocks EGF-induced elongation, must occur prior to activation of protein kinase C.

Treatment of cultures with EGF resulted in a loss of circumferential bands of f-actin and enhancement of cytoplasmic fibers such as those seen in cells migrating away from an explant or into a wound area. Treatment of cultures with INDO either alone or in combination with EGF resulted in a pattern of f-actin labelling of diffuse reticular fibers throughout the cytoplasm. These altered patterns of f-actin distribution within elongated cells in vitro appear to be related to cellular migration, and therefore INDO and/or EGF appear to induce cellular mobility.

Electron microscopy of confluent cultures of polygonal corneal endothelial cells reveals a number of features previously described in native and cultured tissue. Most prominent of these is the characteristic presence of intracellular junctional complexes, resembling both gap- and occludens-type junctions seen in vivo. In culture, these cells are often overlaid by cytoplasmic but not nuclear regions of neighboring cells. This relationship between polygonal cells and the maintenance of apical/basal polarity leads to the conclusion that the observed cellular overlap is somewhat analogous to the extensive intracellular, interdigitization characteristic of the native, differentiated corneal endothelium.

Alteration of endothelial morphology by EGF or INDO, either singly or in combination, included loss of junctions and polarity with the resultant appearance of dedifferentiated cells. Similarly elongated corneal endothelial cells are observed in cultures exposed to PMNs, grown on fibroblastic extracellular matrix, or derived from the hypertrophic tissue characteristic of retrocorneal membranes. In vivo, elongated cells are characteristic of the developing corneal endothelium and mature endothelium migrating into a wound area.

These results demonstrate that pharmacological modulation of corneal endothelial cell shape in vitro results in altered patterns of f-actin labelling and loss of several ultrastructural features characteristic of differentiated cells. By using specific modulators of intracellular messenger systems, two interdependent transduction pathways controlling cell shape and mitotic activity have been identified and can be manipulated.

The two interdependent pathways regulating cell shape, mitosis and presumably the state of differentiation of corneal endothelial cells are depicted in FIG. 1. One pathway, activated by exogenous EGF, most likely acts through a specific receptor causing increased hydrolysis of membrane phosphatidyl inositol to inositol triphosphate and diacylglycerol, which activate protein kinase C. Pharmacological activation of protein kinase C by TPA in these studies appeared to mimic EGF and to lead to elongation of the cells and increased cell division. A second pathway is dependent upon endogenous synthesis of prostaglandin $E_2$, either directly from arachidonic acid or indirectly from diacylglycerol. This pathway, which maintains the polygonal endothelial shape, is mediated by intracellular synthesis of cyclic AMP, since its action is mimicked by direct activators of adenylate cyclase, CTX and forskolin, or by inhibiting endothelial cyclic AMP phosphodiesterase with IBMX. The ability of pertussis toxin to restore polygonal cell shape to EGF- or INDO-treated cultures suggests that an inhibitory G protein is normally associated with endothelial adenylate cyclase in elongated cells. Because CTX prevents EGF- but not TPA-induced elongation, the ability of the cyclic AMP-mediated pathway, presumably through activation of protein kinase A, to block EGF-induced elongation must occur at a step before activation of protein kinase C. However, the EGF- and TPA-induced mitotic effects are potentiated by CTX. Thus, elevated intracellular cAMP has two functional roles in corneal endothelial cells: (1) maintenance of polygonal shape; and (2) enhanced mitosis when activation of protein kinase C occurs and cells elongate. Accordingly, these responses can be modified by binding of an EGF-like compound to a receptor which activates this pathway.

On the basis of these results, it is possible to hypothesize that regulation of the state of corneal endothelial cell differentiation is a complex function of at least two, intracellularly mediated, interacting pathways. The characteristics of the state of differentiation that occur in culture closely resemble different response states of endothelial cells in vivo. The differentiated state is apparently the polygonal-shaped cell performing the physiological functions of the corneal endothelial layer; whereas the dedifferentiated state is the elongated cell which may participate in wound healing in this tissue by migrating into the denuded area. However, further studies on actual corneas was required to demonstrate that manipulation of these pathways can actually be used to both enhance healing and to restore the function of the corneal endothelial cells as a permeability barrier.

EXAMPLE 3

Control of healing and restoration of corneal endothelial cell function using EGF and INDO Animals New Zealand white rabbits were cared for and treated in accordance with the ARVO Resolution on the Use of Animals in Research.

Corneal preparation

New Zealand white rabbits, weighing 2-3 kg, were anesthetized with an intramuscular injection of ketamine and xylazine and then were sacrificed with an overdose of intravenously administered phenobarbital sodium. The eyes were immediately enucleated. For isolated cornea measurements, corneo-scleral buttons were made using standard eye bank procedures. These buttons were then placed endothelial side up in medium in a specular microscope examination chamber. Three media were prepared: M-K medium with EGF (10 ng/ml), M-K medium with EGF (10 ng/ml), and indomethacin (1 $\mu$M), and M-K medium alone. Each group contained eyes from different animals. Corneas were incubated in media for at least one hour prior to wounding.

Wounding of the endothelium of excised corneas

An examination chamber was placed under an eye bank specular microscope (Bio-Optics LSM 2100C) for observation. During the observation period the chamber was placed on a warm water circulating plate through which a heated bath (WESLAB RTE8) circulated warm water that maintained the medium at a constant 37° C. The touch method used to produce the mechanical wounds is briefly described. A 27 gauge stainless steel needle was bent using a pliers so that the needle could be inserted at an appropriate angle along the side of the objective lens. A fine glass needle with a tip diameter of 150 μm was made by a specially designed micropipette puller and affixed onto the tip of the stainless steel needle. The glass tip was inserted into the chamber and positioned under the objective lens. Using a micromanipulator (Stoelting), the needle tip was carefully guided under the specular microscope. An endothelial wound was made with the tip of glass by a gentle and controlled touch to the endothelium. The wound close process (initial wound area about 85 μm$^2$) was observed and continuously recorded with time-lapse videography for six hours.

Analysis.

(1) Wound area

To quantitate the rate of wound closure and changes in the shape of cells around the wound area, the recorded video images were digitized and computer assisted morphometric analysis was performed with a Video Digitization Image Analysis System (BioOptics ECC-2000-2). Each wound area that gave a dark appearance in the specular image was digitized at 1, 5, 10, 20, 40, 60, 90, 120, 150, 180, 210, 240, 300, 330, and 360 min after wounding. Within each of the 3 groups, the mean Wound area for each time point was calculated and used for comparisons.

(2) Shape of the cells near the wound boundary.

The shape of the first row of visible cells around each wound area was analyzed at 1, 50, 100, 150, 200, and 250 minutes after wounding. Seven to seventeen cells surrounding the wound area were arbitrarily chosen and the apices of these cells were digitized. The computer calculated the area, shape factor and other morphologic parameters of each cell automatically. Each cell group was analyzed at 1 and 150 minutes after wounding to compare the rate of shape change in each of the 3 groups. The relative shape change was calculated as:

$$\text{relative shape change (\%)} = \frac{\text{shape factor at 150 minutes} - \text{shape factor at 1 minute}}{\text{shape factor at 1 minute}} \times 100$$

where $4\pi A/P^2$ (P = perimeter, A = area) was used as the shape factor. A decreasing shape factor denotes increasing cell elongation.

(3) Cell migration near the wound boundary

Under each condition in two corneas, the migration distance of the cells near the initial wound border was calculated. A cell in the field which was located as far as possible from the wound was initially identified as a reference cell; this cell was digitized as the origin of the x-y coordinate system. The apices of several cells near the wound boundary at 1 minute and at 150 minutes after wounding were then digitized. The computer calculated the x-y coordinates of the center of gravity of each cell and measured the distance of cell migration between each cell at 1 minute and 150 minutes after wounding by using the following equation:

$$\text{cell migration distance} = \sqrt{(X_{(150)} - X_{(1)})^2 + (Y_{(150)} - Y_{(1)})^2}$$

Figure 2:
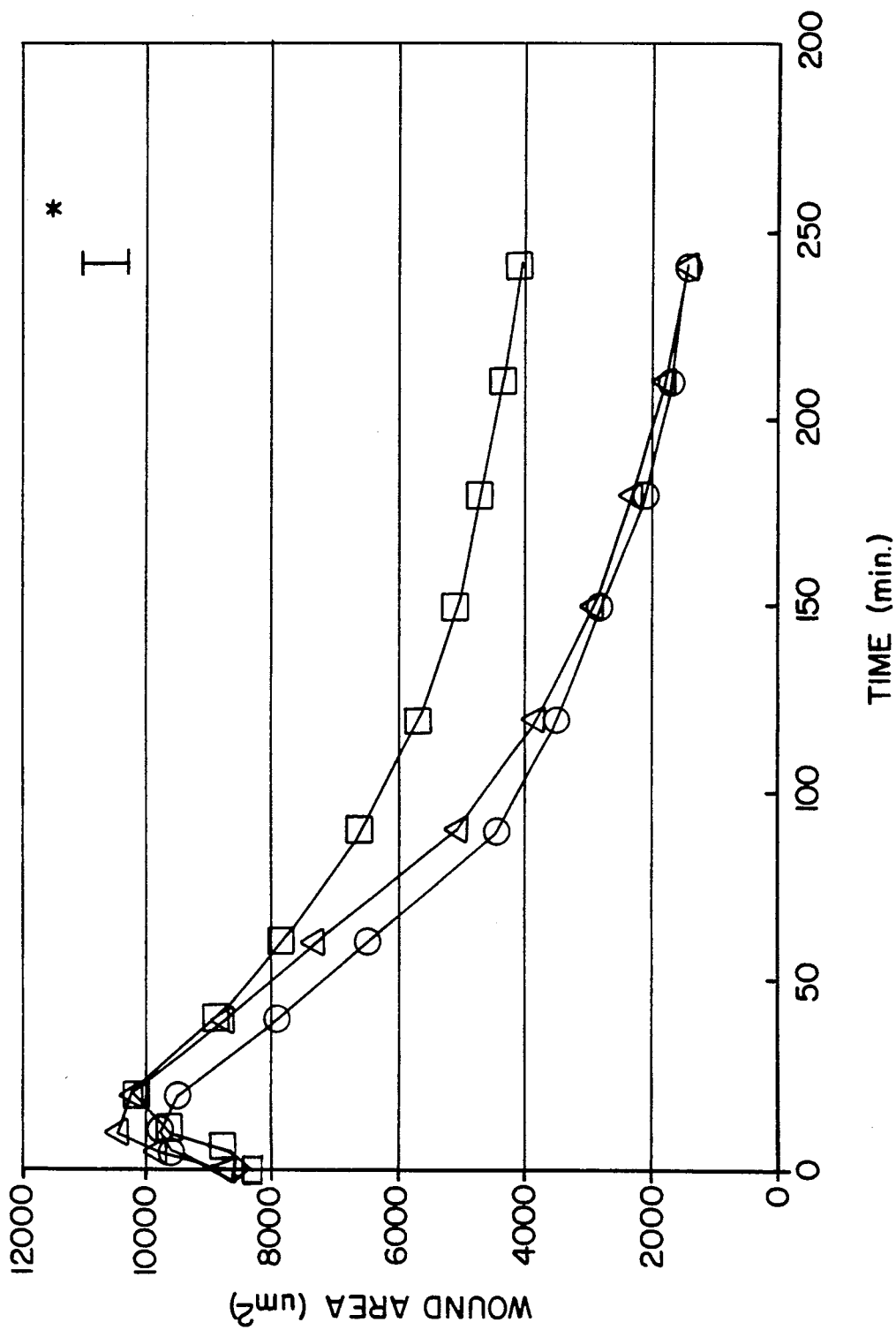
FIG. 2 is a graph of the change in endothelial wound area with time following wounding. The wound area plotted is the mean of five corneas from each group. O: EGF+indomethacin group; Δ: EGF group; []: control group. The vertical bar denotes the standard error of the mean (SEM) for the individual points.

The specular microscopic cell image was clear and distinct for 240 minutes after wounding. After this time the specular microscopic image rapidly degraded and it became difficult to perform the cell analysis. The initial wound area for each of the 15 corneas studied was approximately 8,500 μm$^2$, roughly round in shape, corresponding to an area of about 35 cells. In all cases the wound area increased immediately after wounding, reaching a maximum value at 10 minutes after wounding for the EGF indomethacin group and the EGF group and at 20 minutes after wounding for the control group (FIG. 2). The wound area decreased to 50% of the original size within 100 minutes in the EGF+indomethacin treated group, within 120 minutes in the EGF treated group, whereas the wounded area of the control group decreased to 50% of the original size in about 240 minutes (FIG. 2). During the entire study there was no significant difference between the EGF-+indomethacin and the EGF group in the wound closure time. However, after 90 minutes each groups showed a significant difference from the control group (p<0.005).

To compare the wound closure rates between the various groups, the data from the peak of the area vs. time curve was plotted on a semi-logarithmic scale and a linear regression of log (area) vs. time was performed for each of the three groups of data. The closure rates were then taken as the slope of these linear regression curves. The closure rates for the treated corneas (30.13 μm$^2$/min) were significantly larger than that for the control corneas (17.45 μm$^2$min) (p<0.01) while there was no statistically significant difference between the two treated groups (p=0.4).

(2) Shape of the cells near the wound boundary

Figure 3:
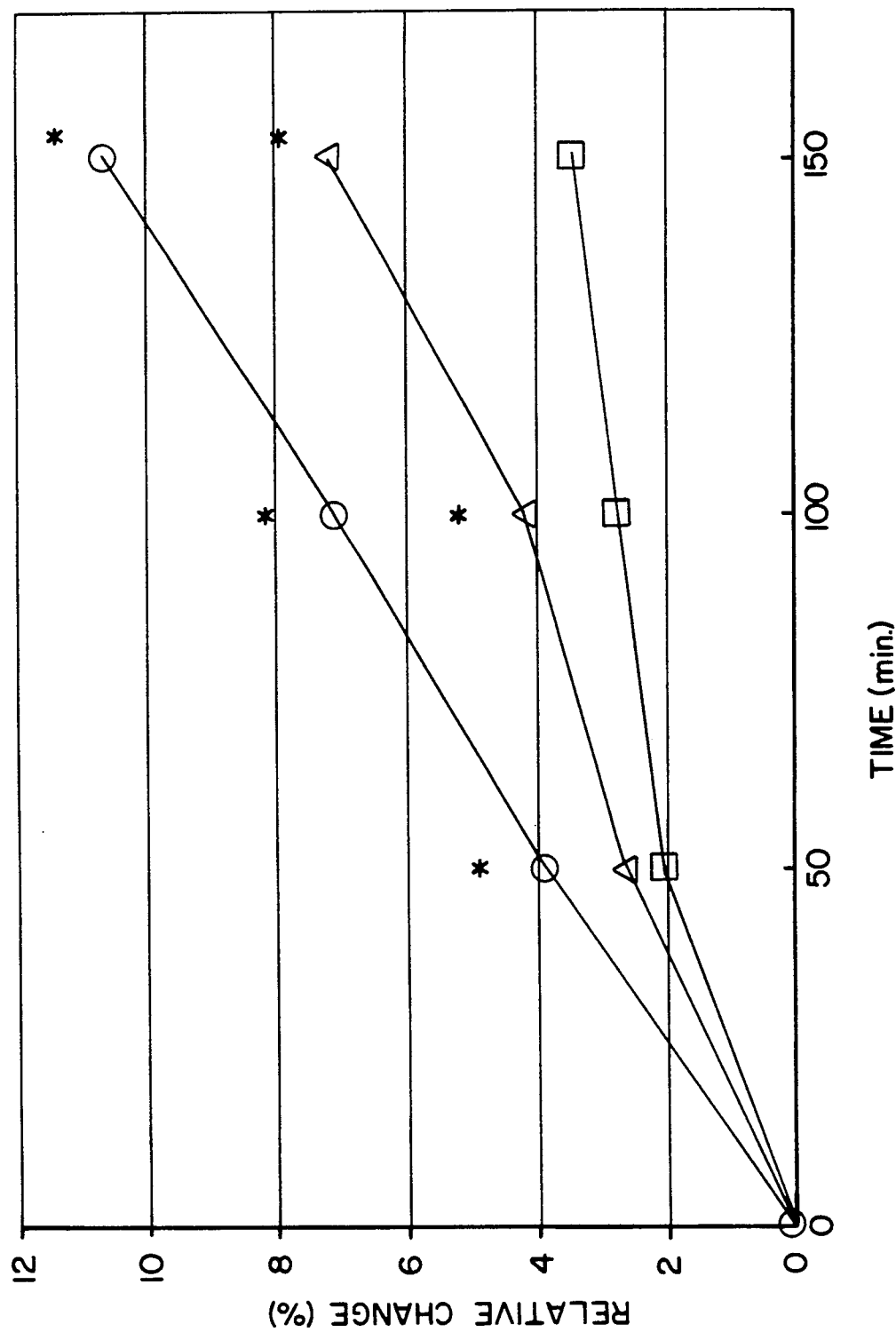
FIG. 3 is a graph of the change in relative average percent change of the shape factor with time following wounding. The EGF+indomethacin group ( O ) is significantly different from the control group ( [] ) at 50, 100, and 150 minutes (p 0.001). The EGF group ( Δ ) is significantly different from the control group at 100 and 150 minutes (p<0.001).

The cell shape and other morphometric parameters were measured at 1, 50, 100, and 150 minutes after wounding. The relative average percent change of the shape factor increased with time in all groups (FIG. 3). At 150 minutes after wounding, both EGF+indomethacin and EGF alone resulted in a greater average percent change of the shape factor that was more than three times greater in EGF+indomethacin and two times greater in EGF alone than in the control group.

One cornea of each group was followed longer than 150 minutes. The peak of the shape change occurred at 150 minutes in the EGF+indomethacin group and in the EGF group and at 200 minutes in the control group. Following these times the rate of shape change decreased in all cases.

(3) Cell migration near the wound boundary

Figure 4A:
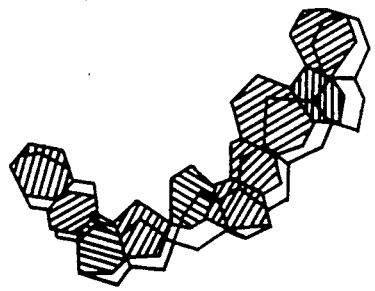
FIG. 4 is the cellular pattern and cell movement of cells near the wound boundary for each group (A, control; B, EGF; C, EGF indo) just after wounding and at 150 minutes after wounding. X denotes the center of the wound.
Figure 4B:
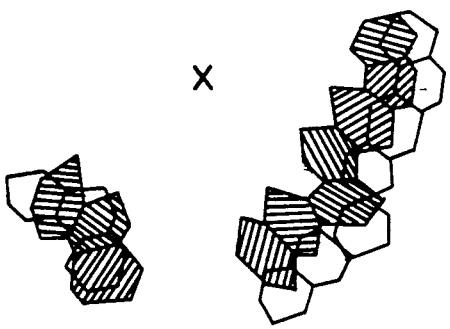
Figure 4C:
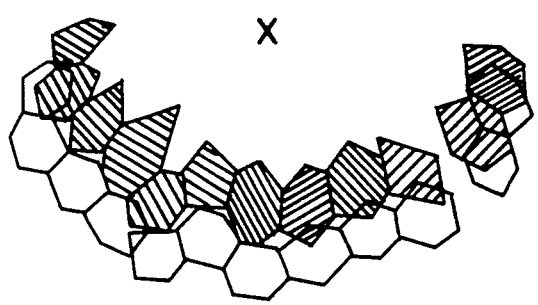

Cellular pattern and cell movement for each group at 150 minutes after wounding is shown in FIG. 4. Most of the cells migrated toward the wound center with the same speed and in the same direction. The average displacement of cells near the wound boundary 150 minutes after wounding was approximately 15 μm for EGF+indomethacin, 16 μm for EGF alone, and 7 μm for the control. The cells near the wound boundary in the EGF+indomethacin and the EGF groups migrated significantly more than those in the control group.

However, there was no significant difference between the EGF+indomethacin and the EGF groups.

The possible beneficial effects of EGF on the wound healing process in the intact corneal endothelium had not been shown prior to these studies, although it had been reported that EGF and indomethacin promote mitosis and cell elongation in cultured rabbit corneal endothelial cells. It was not known if these effects would also be present in the intact corneal endothelium, nor whether EGF or EGF+indomethacin could influence endothelial mobility and morphology in an intact cornea during the endothelial wound closure process.

EGF interacts with specific, high affinity cell surface receptors that are present in a wide variety of cultured cells including corneal cells, human fibroblasts, lens cells, human glial cells, human epidermoid carcinoma cells, 3T3 cells, and granulosa cells. It has been shown that the time course of association of radiolabeled EGF to cat corneal endothelium was complete after approximately 120 minutes at 22° C., and that there were 4,000 receptors per cell. In the present study, a sclerocorneal button was maintained in medium containing EGF at 37° C. from 1 hour before wounding until the completion of the experiments, so one can assume binding of EGF to the receptor and activation during this period.

The effects of EGF and indomethacin on corneal endothelial cell shape are demonstrated in examples 1 and 2. It was theorized from this data that endogenous synthesis of prostaglandin $E_2$ ($PGE_2$) is an important factor for the maintenance of the normal, polygonal endothelial cell shape and that if the synthesis of $PGE_2$ is blocked, an extraordinary change in the cell shape occurs which is potentiated by EGF. The cells become even more fibroblastic-like in culture. This data showed that EGF promotes mitosis and elongation in cultured rabbit corneal endothelial cells, and when cells are cultured in the presence of EGF (10 ng/ml) and indomethaoin (1 $\mu$M), elongation was more pronounced with maximum axes of 60 $\mu$m, compared with 33 $\mu$m for untreated cells.

The presence of either EGF (10 ng/ml)+indomethacin (1 $\mu$M) or EGF (10 ng/ml) alone in the M-K medium significantly increased migration of cells near the wound boundary and shortened the wound closure time as compared with the control group. However, there was no significant difference between the EGF+indomethacin group and the EGF group in either wound closure time or the average rate of the migratory cells. Therefore, the effect on cell migration must be primarily due to EGF.

The peak of the cell shape change occurred between 150 to 200 minutes. Following these times the cell shape change progressively decreased and the cells approached their original shapes. Comparing wounds between 0.7 and $2.0 \times 10^5$ $\mu m^2$ is area made by scraping the endothelium with a length of 4-0 nylon monofilament and wounds in excised corneas, 8,500 $\mu m^2$ in area, differences in the time to reach the maximum rate of change of cell shape between in vivo and excised cornea is probably due to the difference in the size of the original wound produced.

In most cell culture systems, increased DNA synthesis begins approximately 15 hours after the addition of EGF and reaches a maximum at about 22 hours. In this study, endothelial wounds treated with EGF were closed to 80% of the original size within 250 minutes after wounding. Therefore, it is unlikely that mitosis has contributed to the wound closure process. Instead, the data demonstrate the closure process proceeds with elongation and migration of cells, without cell division.

In summary, both growth factors such as EGF and non-steroidal anti-inflammatories such as indomethacin are useful in promoting healing of traumatized human corneal endothelium as determined from effects on intact rabbit corneal endothelium.

Modifications and variations of the method and compositions of the present invention for enhancing healing and restoration of function of corneal endothelium will be obvious to those skilled in the art from the foregoing detailed description of the invention. Such modifications and variations are intended to come within the scope of the appended claims.

We claim:

1. A method for enhancing healing and restoring function of corneal endothelial tissue comprising manipulating migration, elongtion, and spreading of corneal endothelial cells by administering to corneal endothelial cells a composition wherein the active agent consists of an EGF-like growth factor which alters cell function by binding to a specific cell surface receptor, wherein said composition is administered in a pharmaceutically acceptable carrier for intraocular administration in an amount producing a concentration at the corneal endothelial cells of from approximately one and up to 50 ng EGF-like compound/ml solution contacting the corneal endothelial cells.

2. The method of claim 1 wherein 1 wherein the growth factor is selected from the group consisting of epidermal growth factor-like compounds, biologically active derivatives and homologous of epidermal growth factor, biologically active fragments of epidermal growth factor, and combinations thereof.

3. The method of claim 1 wherein an effective amount of the composition is that amount which promotes closure of corneal endothelial tissue and restoration of permeability function of the corneal endothelial tissue.

4. The method of claim 3 further comprising measuring corneal clarity to determine restoration of permeability function.

5. The method of claim 3 further comprising measuring corneal thickness to determine restoration of permeability function.

6. The method of claim 1 further comprising providing a nutritive solution for storing corneas.

7. The method of claim 1 wherein the composition is administered to the cornea prior to injury.

8. The method of claim 1 further comprising administering the composition in an intraocular irrigating solution.

9. The method of claim 8 wherein the composition is administered to the cornea at the time of or following injury or surgery.

10. The method of claim 1 further comprising providing growth factor in a controlled release material.

11. The method of claim 1 wherein the EDG-like compound is administered intraocularly to a concentration of approximately 10 ng EGF-like compound/ml of solution contacting the corneal endothelial cells.

* * * * *